(12) United States Patent
Shankar et al.

(10) Patent No.: US 9,810,653 B2
(45) Date of Patent: Nov. 7, 2017

(54) INTEGRATED SMO GAS SENSOR MODULE

(71) Applicant: STMicroelectronics Pte Ltd, Singapore (SG)

(72) Inventors: Ravi Shankar, Singapore (SG); Olivier Le Neel, Singapore (SG); Tien-Choy Loh, Singapore (SG); Shian-Yeu Kam, Singapore (SG)

(73) Assignee: STMICROELECTRONICS PTE LTD, Singapore (SG)

( * ) Notice: Subject to any disclaimer, the term of this patent is extended or adjusted under 35 U.S.C. 154(b) by 559 days.

(21) Appl. No.: 14/334,572

(22) Filed: Jul. 17, 2014

(65) Prior Publication Data

US 2016/0018356 A1 Jan. 21, 2016

(51) Int. Cl.
G01N 27/12 (2006.01)

(52) U.S. Cl.
CPC ............ *G01N 27/12* (2013.01); *G01N 27/123* (2013.01); *G01N 27/125* (2013.01); *G01N 27/128* (2013.01)

(58) Field of Classification Search
CPC .... G01N 27/12; G01N 27/123; G01N 27/125; G01N 27/128; G01N 27/129; G01N 27/227
See application file for complete search history.

(56) References Cited

U.S. PATENT DOCUMENTS

| 4,485,667 | A | | 12/1984 | Lalauze et al. |
| 5,528,225 | A | | 6/1996 | Sakai et al. |
| 5,605,612 | A | * | 2/1997 | Park ........................ G01N 27/12 204/429 |
| 6,051,854 | A | * | 4/2000 | Vigna ..................... G01N 27/12 204/424 |
| 7,963,147 | B2 | | 6/2011 | Jun et al. |
| 8,436,426 | B2 | | 5/2013 | Le Neel et al. |
| 8,470,147 | B2 | | 6/2013 | Nair et al. |
| 8,644,053 | B2 | | 2/2014 | Le Neel |

(Continued)

FOREIGN PATENT DOCUMENTS

WO 2013/128186 A1 9/2013

OTHER PUBLICATIONS

Figaro, "TGS 2611—for the detection of Methane," Product Information, Feb. 2005, 2 pages.

(Continued)

*Primary Examiner* — Paul West
(74) *Attorney, Agent, or Firm* — Seed IP Law Group LLP

(57) ABSTRACT

Miniature resistive gas detectors incorporate thin films that can selectively identify specific gases when heated to certain characteristic temperatures. A solid state gas sensor module is disclosed that includes a gas sensor, a heater, and a temperature sensor, stacked over an insulating recess. The insulating recess is partially filled with a support material that provides structural integrity. The solid state gas sensor module can be integrated on top of an ASIC on a common substrate. With sufficient thermal insulation, such a gas detector can be provided as a low-power component of mobile electronic devices such as smart phones. A method of operating a multi-sensor array allows detection of relative concentrations of different gas species by either using dedicated sensors, or by thermally tuning the sensors to monitor different gas species.

28 Claims, 18 Drawing Sheets

(56) References Cited

U.S. PATENT DOCUMENTS

| | | |
|---|---|---|
| 9,000,542 B2 | 4/2015 | Loh et al. |
| 2006/0231422 A1 | 10/2006 | Rhodes et al. |
| 2009/0243003 A1 | 10/2009 | Renna et al. |
| 2010/0050744 A1 | 3/2010 | Petrovic |
| 2012/0049997 A1* | 3/2012 | Lim .................. H01L 21/76834 338/308 |
| 2012/0168882 A1 | 7/2012 | Cherian et al. |
| 2012/0171713 A1 | 7/2012 | Cherian et al. |
| 2013/0301052 A1 | 11/2013 | MacGregor et al. |
| 2015/0323510 A1* | 11/2015 | Huynh ................ H01L 23/3157 73/23.34 |

OTHER PUBLICATIONS

Korotcenkov, "Metal Oxides for Solid-State Gas Sensors: What Determines Our Choice?" *Materials Science and Engineering B* 139, 23 pages, 2007.

"MQ-4 Semiconductor Sensor for Natural Gas," Henan Hanwei Electronics Co., Ltd, 3 pages.

Sharma et al., "Investigation of stability and reliability of tin oxide thin-film for integrated micro-machined gas sensor devices," *Sensors and Actuators B* 81:9-16, 2001.

* cited by examiner

INTEGRATED SMO GAS SENSOR MODULE

BACKGROUND

Technical Field

The present disclosure generally relates to the field of microelectronic sensors and, in particular, gas sensors integrated with circuitry on a semiconductor substrate.

Description of the Related Art

Miniature solid state gas sensors integrated with microelectronics allow construction of an "electronic nose" that can selectively detect the presence of, for example, toxic substances such as carbon monoxide (CO), or vapor associated with controlled substances such as ethanol.

It is well known that thin films made of certain metal materials, for example, semiconductor metal oxides (SMOs), experience a change in resistivity when they are exposed to certain gases at certain temperatures, as described in U.S. Pat. No. 4,485,667. Typically, SMO sensors operate at temperatures between 200 and 500 C. One such example of an SMO material is tin oxide ($SnO_2$) which, when heated to 380 C-400 C and then exposed to methane gas, experiences a chemoresistive reaction (1) that produces free electrons, thereby altering the resistivity of the tin oxide film:

$$SnO_2 + CH_4 \rightarrow CO_2 + H_2O + e^- \qquad (1)$$

SMO sensors based on $SnO_2$ or nickel oxide (NiO) are currently manufactured and sold by companies such as Hanwei Electronics Co., Ltd. of Zhengzhou in the Henan province of China, and Figaro Engineering, Inc. of Glenview, Ill.

By integrating a tin oxide thin film with an integrated circuit and a heating element, it is possible to construct an electronic gas detector suitable for use in a home or industrial environment, for example, or a portable breathalizer for use by law enforcement officers. Integration of chemical sensors with microelectronics on a common semiconductor die is described in U.S. Patent Application Publications 2012/0168882 and 2012/0171713, to Cherian and LeNeel, a co-inventor of this patent application, which publications are hereby incorporated by reference in their entirety.

One problem that arises in designing SMO thin film gas sensors is that the associated heaters tend to consume large amounts of electrical power to heat the SMO thin films to operating temperatures in the range of about 100 C-500 C, so the heaters tend to quickly drain the battery of the portable sensor device.

Another challenge is that the SMO sensors may have difficulty distinguishing between two gases. For example, carbon monoxide (CO) sensors also tend to be sensitive to hydrogen gas ($H_2$). Thus, it is desirable to operate the sensor only within a small temperature range around the temperature at which the sensor has peak sensitivity to the particular gas of interest. Furthermore, instead of heating one sensor to different temperatures to detect different gases, it would be advantageous to dedicate specific sensors to specific gases. Alternatively, it would be advantageous to assemble multiple data points from a plurality of sensors that are all tuned to a particular gas, to increase specificity and to obtain more precise measurements.

Another challenge lies in providing thermal insulation for the gas sensors so that neighboring devices are not heat-damaged by such extreme temperatures. In some environments, heating the SMO sensor to temperatures in the range of 100 C-400 C can pose a safety risk—for example, if there exists a sufficient concentration of an ambient gas for which the combustion temperature is within the range of the operating temperature of the sensor. Some existing SMO sensor products include insulating layers between the heater and the substrate. U.S. Patent Application Publication 2009/0243003, entitled "Manufacturing Method of a Gas Sensor Integrated on a Semiconductor Substrate," assigned to the same assignee as this patent application, addresses thermal insulation by forming an insulating cavity buried in the semiconductor substrate, the cavity being filled with air. However, although air is an effective thermal insulator, a substrate having an air cavity is generally structurally unstable, and prone to collapse. Thus, the depth of such an air cavity may be structurally limited.

BRIEF SUMMARY

A miniature resistive SMO gas sensor module as described herein includes an SMO gas sensor, a resistive heater, and a resistive temperature sensor integrated with an application specific integrated circuit (ASIC). The gas sensor, heater, and temperature sensor are stacked adjacent to an insulating cavity that is structurally supported by pillars. In one example, the pillars are made of polyimide. The resistive heater is located next to the SMO gas sensor to conserve battery power. The resistive temperature sensor is placed in close proximity to the SMO gas sensor to ensure accurate temperature measurements. Electrical tests using pulsed signals indicate that use of the disclosed heat confinement structure lowers power consumption from 900 mW to less than about 5 mW.

An exemplary method of fabricating the miniature resistive SMO gas sensor module incorporates the resistive devices with an ASIC after the ASIC is formed. In one embodiment, the SMO gas sensor module, having feature sizes in the range of about 1 μm-10 μm, is constructed on top of a completed ASIC that is fabricated using 0.13 μm or 0.18 μm process technology. Such an integration scheme is made possible by restricting thermal processing of the SMO gas sensor module to temperatures lower than about 400 C. One advantage of integrating the gas sensor module closely with the ASIC is that less wiring is required between the ASIC circuitry and the gas sensor components. With less wiring, there is less signal noise, and less power is dissipated.

A method of operating a gas sensor array made up of a plurality of gas sensor elements facilitates detection of relative concentrations of different gas species, either by using dedicated sensors, or by thermally tuning the sensors to monitor different gas species.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

DETAILED DESCRIPTION

Figure 1A:
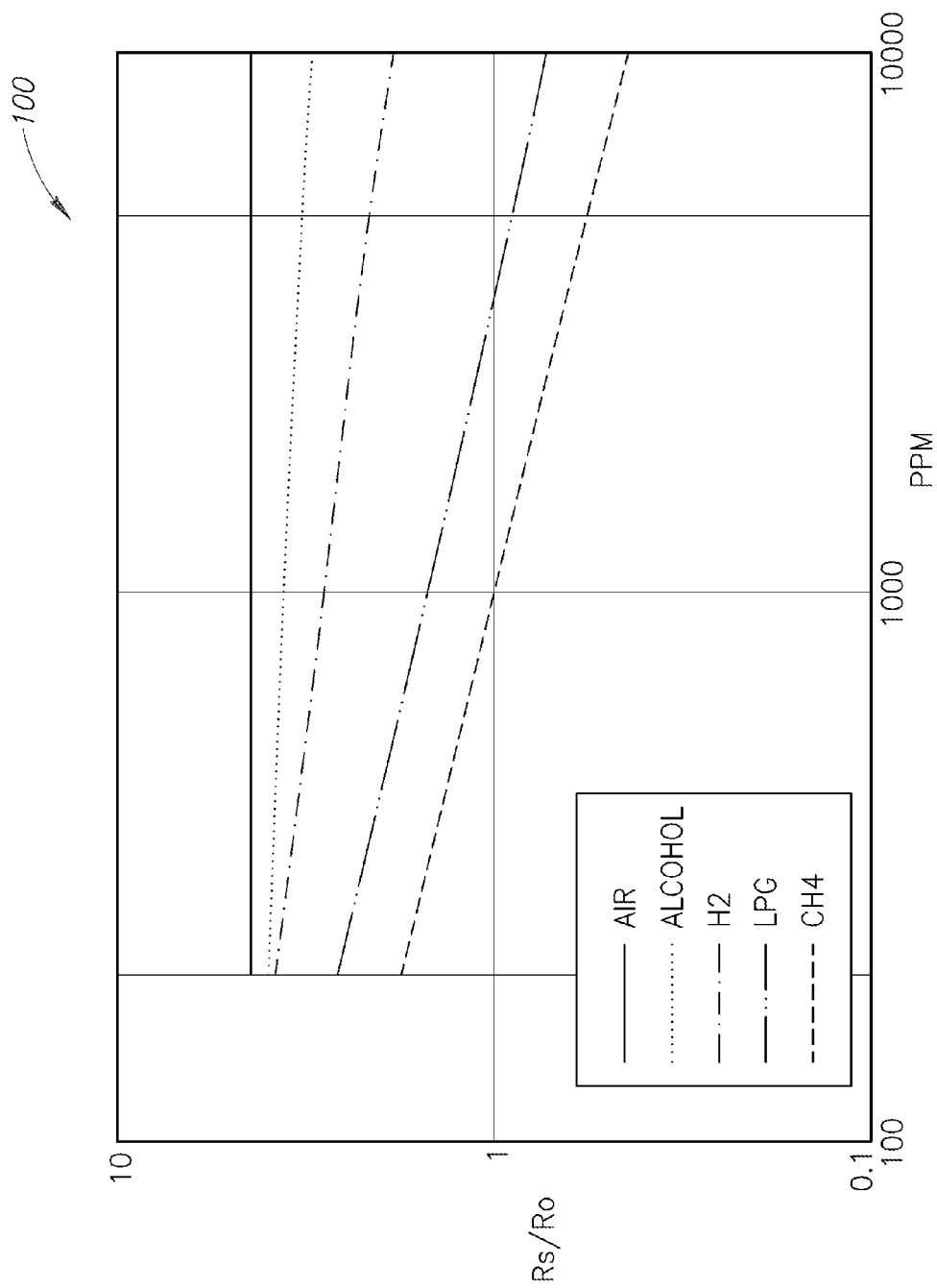
FIG. 1A is a plot of SMO gas sensor responses to different gases according to the prior art.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting substrates, whether or not the components are coupled together into a circuit or able to be interconnected. Throughout the specification, the term "layer" is used in its broadest sense to include a thin film, a cap, or the like and one layer may be composed of multiple sub-layers.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in-situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence typically followed by an etch process. Alternatively or additionally, photoresist can also be used to pattern a hard mask (e.g., a silicon nitride hard mask), which, in turn, can be used to pattern an underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to gas sensors that have been produced; however, the present disclosure and the reference to certain materials, dimensions, and the details and ordering of processing steps are exemplary and should not be limited to those shown.

Figure 1B:
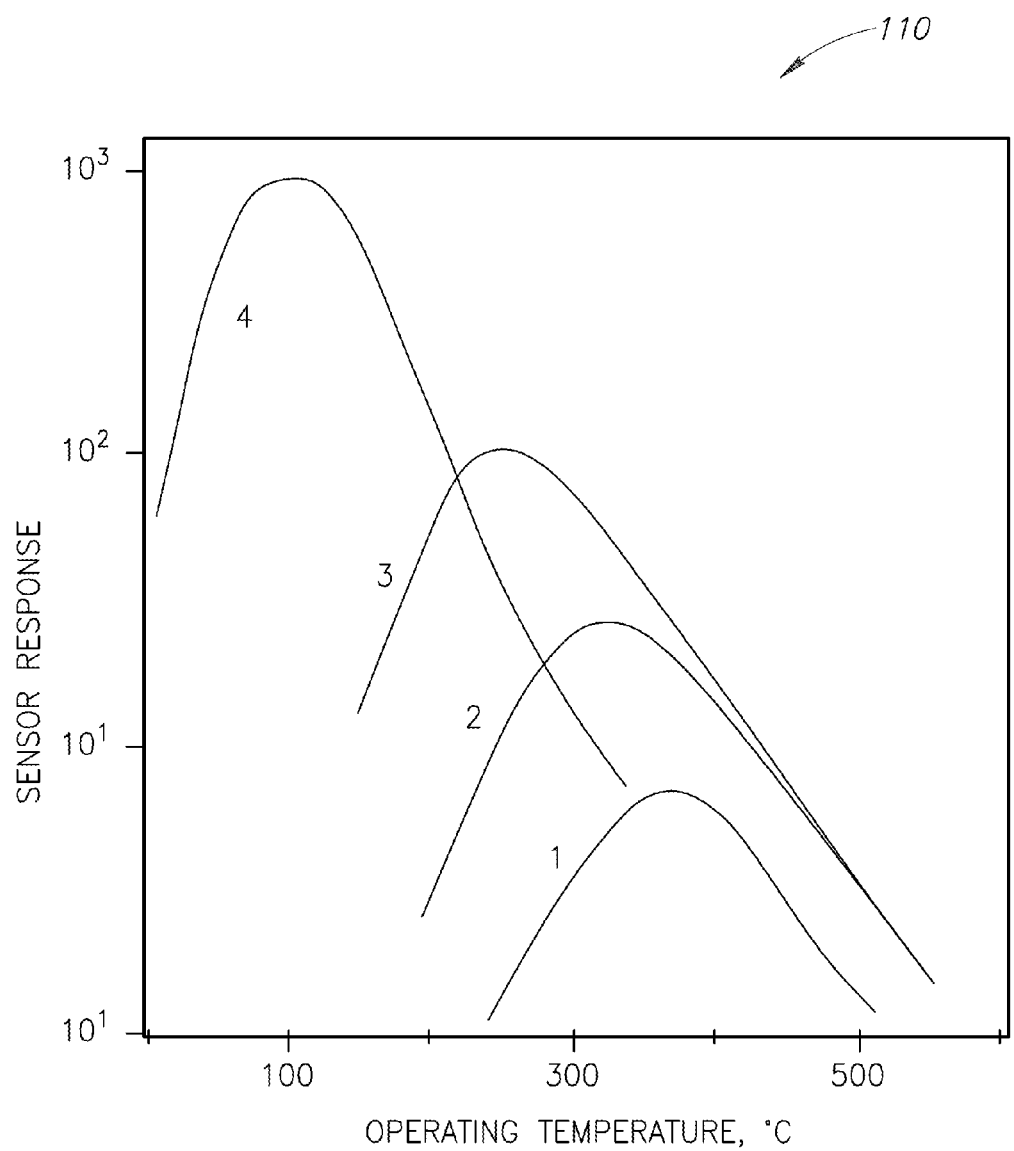
FIG. 1B is a plot of SMO gas sensor response as a function of temperature, according to the prior art.

FIGS. 1A and 1B show sensitivity characteristics of tin oxide ($SnO_2$) SMO gas sensors. The resistance of a thin film of tin oxide changes in the presence of various gases of interest. Such a change occurs at temperatures within the range of about 100 C-400 C, and in the presence of oxygen. FIG. 1A is a log-log plot 100 derived from a data sheet for existing discrete sensors manufactured by Figaro USA, Inc. of Arlington Heights, Ill. FIG. 1A shows normalized resistance vs concentration in parts per million of the tin oxide sensor for five different gases. For example, the bottom curve shows that the resistance of a tin oxide thin film changes dramatically with concentration of methane gas ($CH_4$), while the top two curves show that the resistance of the tin oxide thin film hardly varies with concentrations of air or ethanol. Thus, tin oxide is most sensitive to detect methane with little interference from ethanol, for example. The tin oxide sensor is also sensitive to liquid petroleum gas (LPG), commonly known as propane or iso-butane, and hydrogen gas ($H_2$), which correspond to the next two steepest curves, after methane.

FIG. 1B shows a log-linear plot 110 of a tin oxide sensor response to carbon monoxide gas (CO) vs. operating temperature in degrees C. It is clear that the response at about 100 C is about 100 times greater than the response at 350 C. Thus, the tin oxide sensor is highly temperature dependent in this example. In general, it is found that the strongest response of the tin oxide sensor to each target gas species occurs at a different heater temperature. The ability to detect gases accurately using an SMO sensor thus requires excellent temperature control. Consequently, to make an SMO-based gas sensor, it is important to incorporate a heater as well as an accurate temperature sensor to provide feedback to control the heater. Because the relevant temperatures are so hot, it is also desirable that the heater will confine heating to a localized region during sensing.

Figure 2:
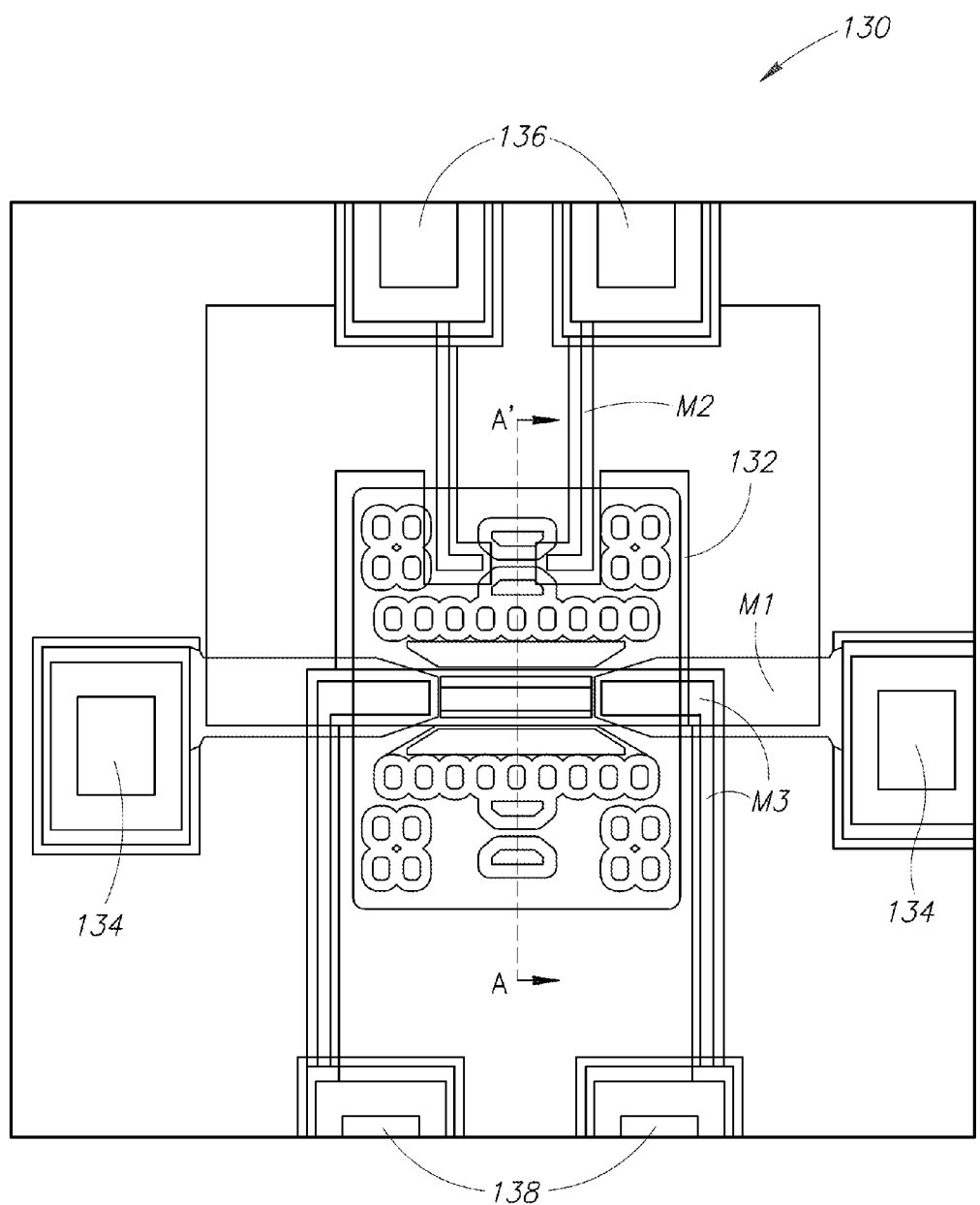
FIG. 2 is a top plan view of a solid state gas sensor module according to one embodiment described herein.

FIG. 2 shows a top plan view of a solid state gas sensor module 130, according to one embodiment, in which a temperature sensor and a heater are co-located with the gas sensor, and a structurally stable heat confinement structure is provided in the sensing area. The solid state gas sensor module 130 as shown in FIG. 2 includes a sensor region 132, heater contacts 134 at metal 2, temperature sensor contacts 136 at metal 3, and SMO sensor contacts 138 at metal 4.

Figure 3:
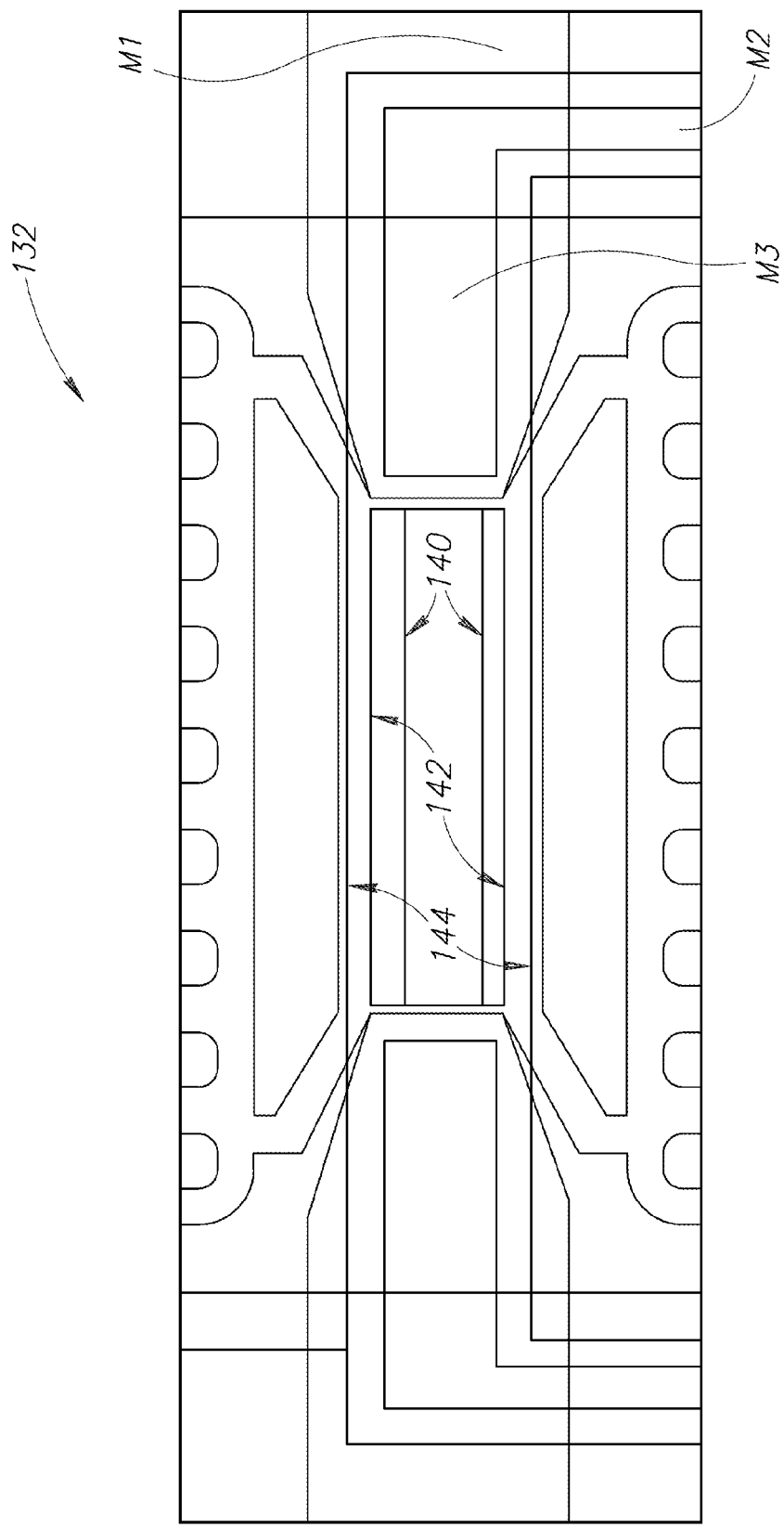
FIG. 3 is a magnified view of the solid state gas sensor module shown in FIG. 2.

FIG. 3 shows a magnified view of the central area of the sensor region 132 of the solid state gas sensor module 130, according to one embodiment. The sensor region 132 as shown has an active sensing area of about 50×50 µm². The sensor region 132 includes three resistive components arranged as a stack of thin films: a heater 140 measuring 90×20 µm, a temperature sensor 142 measuring 100×30 µm, and an SMO sensor 144, measuring 110×40 µm. The SMO sensor 144 has a film thickness of about 200 nm, which is much thinner than conventional SMO sensors that use bulk films typically having thicknesses within the range of about 100 µm to 1 mm. The sensors are formed vertically adjacent to one another, at three different layers, wherein the temperature sensor 142 is positioned above the heater 140 and the SMO sensor 144 is positioned above the temperature sensor. Because the component films are very thin, the different layers are partially transparent. The heater 140 is made of a tantalum aluminum (TaAl) thin film resistor, having a sheet resistance of about 160 Ω/square. The heater 140 heats the SMO sensor 144 to a temperature within the range of about 100 C-400 C while consuming less than 50 mW of power. The temperature sensor 142 is made of an 80/20 alloy of chromium silicate (CrSi), and has a sheet resistance of about 980 kΩ/square. The SMO sensor 144 is made of undoped tin oxide ($SnO_2$), and has a sheet resistance of about 900 kΩ/square. Such a tin oxide film can be doped, for example, with palladium to sense carbon monoxide, or with platinum to sense hydrogen gas, or with silver to sense hydrogen sulfide ($H_2SO_4$). Although process integration of CrSi resistive thin films was disclosed by the present inventors in U.S. Pat. No. 8,436,426, assigned to the same assignee as the present patent application, integrating sensors made of $SnO_2$, CrSi, and TaAl into a common sensor module has not been disclosed.

Figure 4:
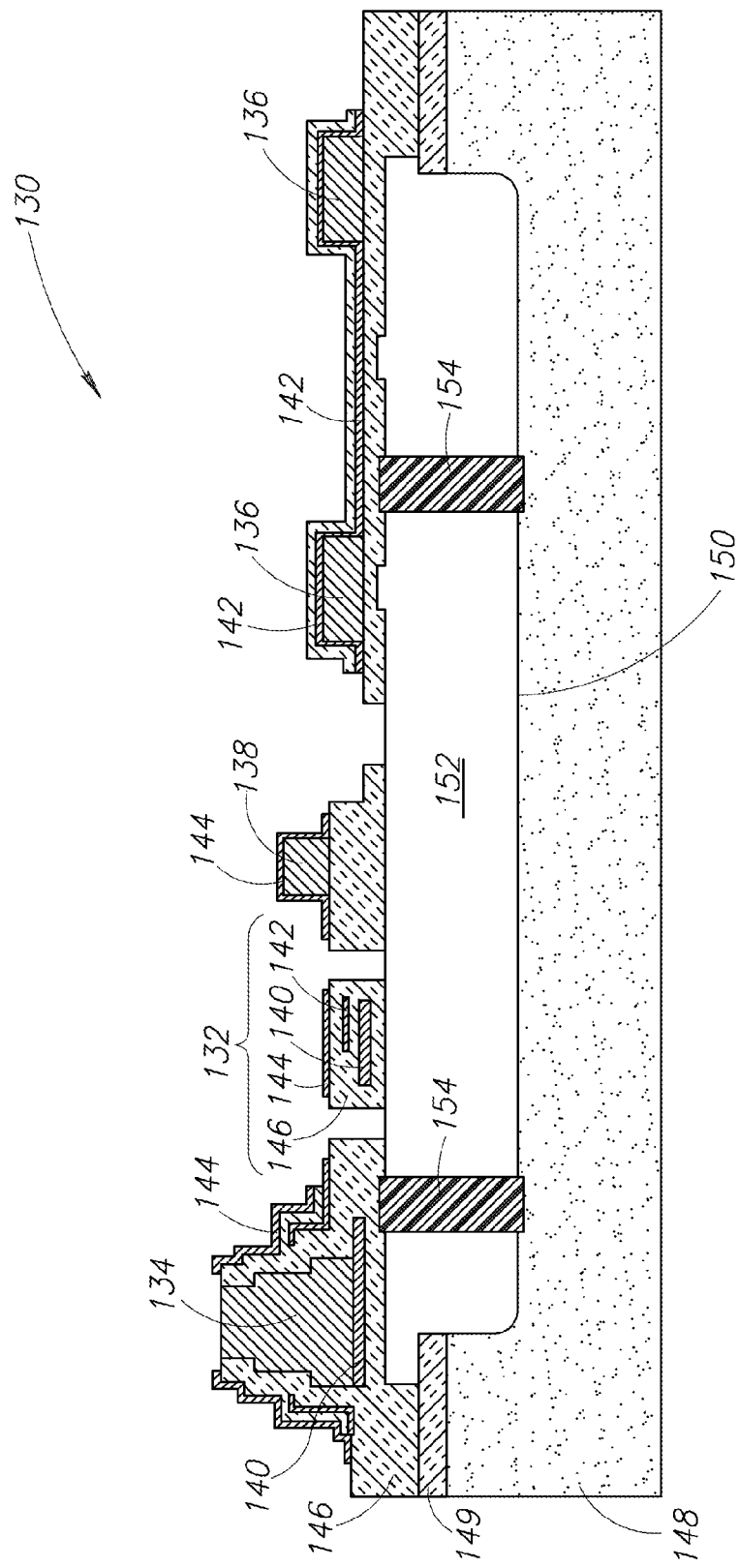
FIG. 4 is a composite cross-sectional view of the solid state gas sensor module shown in FIGS. 2 and 3.

FIG. 4 shows a composite cross-sectional view of the solid state gas sensor module 130 taken along the cut lines A-A' shown in FIG. 2, together with contacts 134, 136, and 138 shown in the same cut plane as the sensor region 132, for convenience. The sensor region 132 includes the three stacked sensors 140, 142, and 144, separated by insulating layers 146. The insulating layers 146 can be made of silicon nitride, for example. The temperature sensor contacts 136 are shown to the far right of the sensor region 132. An SMO sensor contact 138 is shown to the right of and adjacent to the sensor region 132, and the heater contact 134 is shown to the left of the sensor region 132. The solid state gas sensor module 130 is formed on a substrate 148 made of, for example, silicon or glass. A silicon dioxide layer 149 separates the substrate 148 from the insulating layers 146. The solid state gas sensor module 130 further includes a thermal insulation structure 150 formed in the substrate 148. Silicon, polyimide, and air were evaluated as materials for use in the thermal insulation structure 150, using simulations of integrated circuit structures. Air, having the lowest thermal conductivity of the three materials, at 0.001 W/mK, is preferred to occupy as much of the thermal insulation structure 150 as possible. Polyimide also has a low thermal conductivity, of about 0.15 W/mK. Silicon, on the other hand, has a thermal conductivity 1000 times greater than polyimide, at 150 W/mK. Based on the simulations, the thermal insulation structure 150 was designed to include an air gap 152 and support pillars 154 made of polyimide that structurally support the solid state gas sensor module 130. The thermal insulation structure 150 confines heat within the solid state gas sensor module 130, thus allowing a high temperature to be maintained in the sensor region 132, with low power input.

Figure 5:
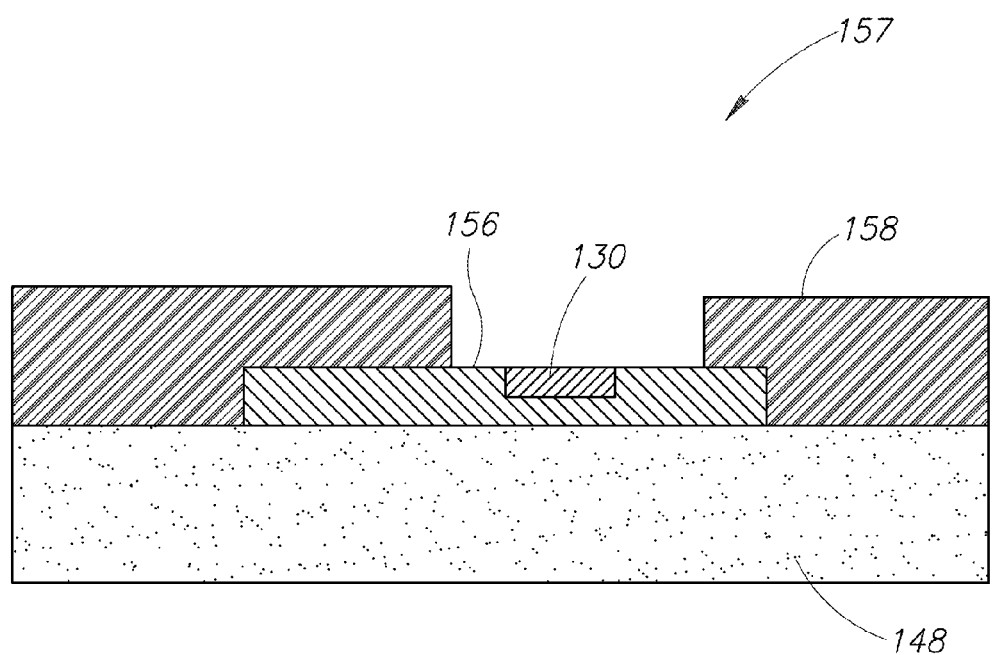
FIG. 5 is a cross-sectional view of a solid state gas sensor module integrated on top of a completed ASIC chip.

With reference to FIG. 5, in one embodiment, the substrate 148 contains control circuitry; for example, an application specific integrated circuit (ASIC) 156. The ASIC 156 includes memory and one or more microprocessors programmed to operate the solid state gas sensor module 130. The ASIC 156 is communicatively coupled to the heater 140, the temperature sensor 142, and the SMO sensor 144, thus allowing the control circuitry within the ASIC 156 to exchange signals with the three thin film components of the solid state gas sensor module 130. For example, the ASIC 156 can receive data signals from the temperature sensor 142 and the SMO sensor 144 and, in response, transmit control signals to the heater 140. ASICs and sensors integrated into a common chip are well known in the art, as disclosed in U.S. Patent Publication No. 2012/0171713, U.S. Patent Publication No. 2012/0168882, and U.S. Pat. No. 8,644,053.

In some embodiments, one or more components of the solid state gas sensor module 130 can be integrated directly into a top layer of the ASIC 156 to create an SMO/ASIC digital sensor module 157. It is possible to integrate the solid state gas sensor module 130 after the ASIC is formed in the substrate 148 if the processing steps used to form the solid state gas sensor module 130 do not exceed process temperatures above about 400 C. The thermal insulation structure 150 helps to prevent heat generated in the sensor region 132 of the solid state gas sensor module 130 from affecting control circuitry in the substrate 148. In addition, a thick oxide dielectric layer, e.g., 5 microns or more, can be used to separate the ASIC 156 from the solid state gas sensor module 130. One advantage of integrating the sensor with the ASIC is that direct connections between the solid state gas sensor module 130 and the ASIC 156 avoid power losses that would otherwise occur in wiring used to couple the two devices. The SMO/ASIC digital sensor module 157 has a surface area in the range of about 1 mm²-4 mm², of which the sensing area is in the range of about 50×50 µm² to about 100×100 µm². Typically, the ASIC uses a more advanced technology with smaller device dimensions than that of the solid state gas sensor module 130. For example, the ASIC may be designed at the 0.18 µm or 0.13 µm technology node, while the sensor structures are in the range of 1 µm-10 µm. The ASIC 156 can be protected by a cap 158 that has an opening to expose the sensing area.

Figure 6A:
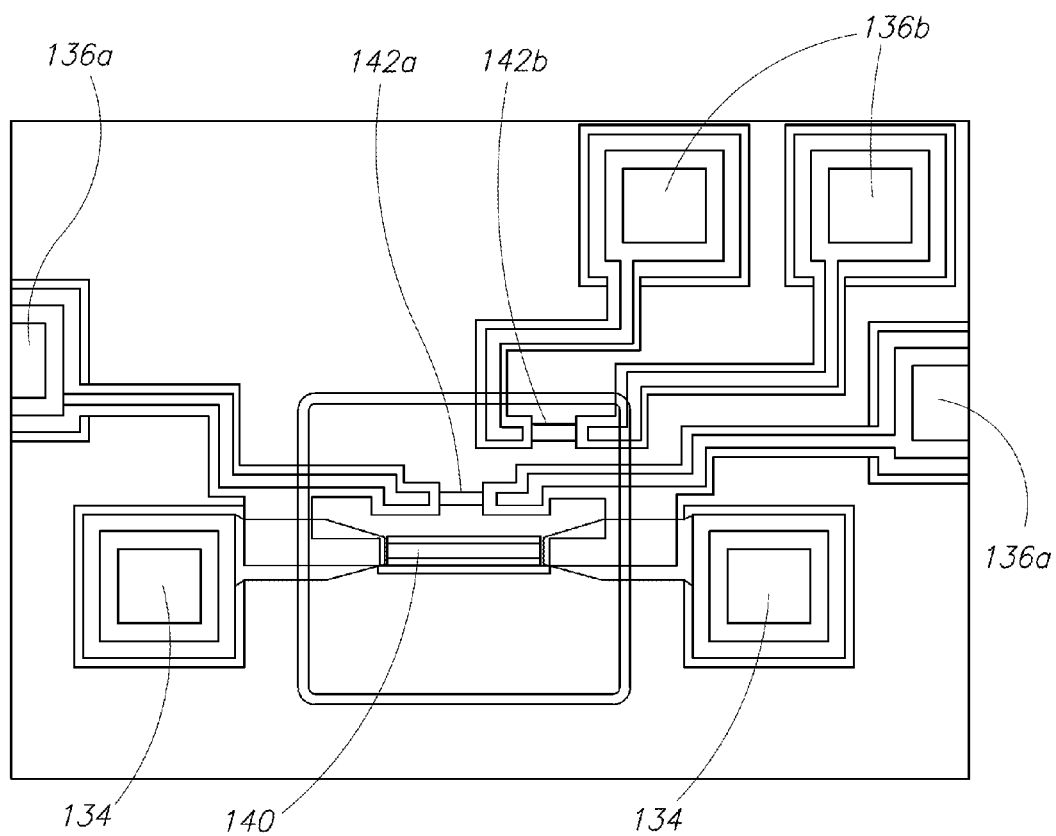
FIG. 6A is a top plan view of a heater test module as described herein.
Figure 6B:
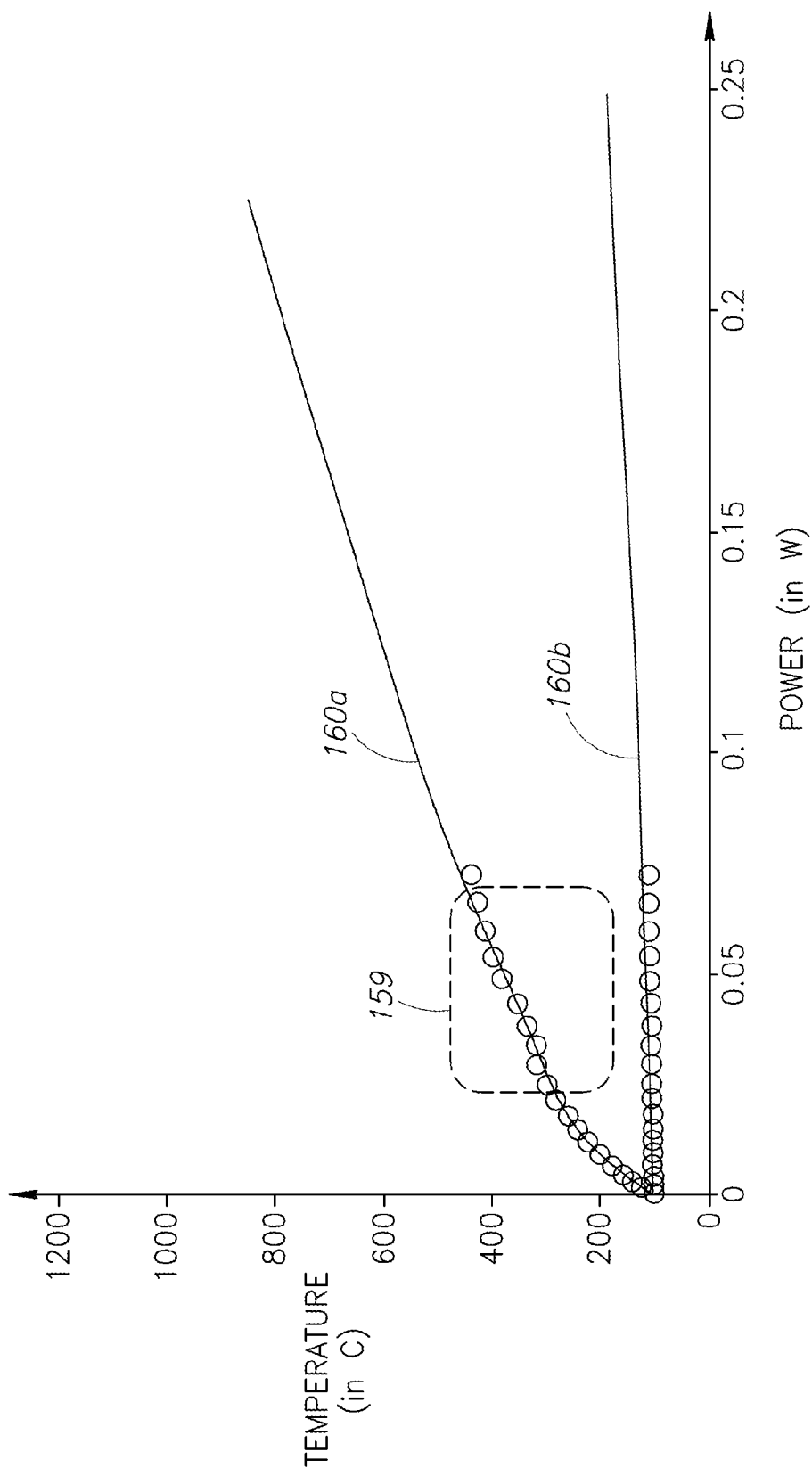
FIG. 6B is a plot of measured heater temperatures as a function of power applied to the heater shown in FIG. 6A.

Heat confinement tests were conducted using one embodiment of the heater 140 adjacent to the thermal insulation structure 150, and temperature sensors 142a and 142b configured as shown in FIG. 6A. The heater 140 was electrically energized at various power levels via the heater contacts 134. In response, the temperature sensor 142a, located adjacent to the heater 140, and the temperature sensor 142b, located a short distance away from the heater 140, near the perimeter of the sensor region 132, were probed via the temperature sensor contacts 136a and 136b, respectively. FIG. 6B shows both sets of temperature data, wherein the curve 160a represents data from the temperature sensor 142a next to the heater 140, and the curve 160b represents data from the remote temperature sensor 142b. The curve 160a shows that temperatures 250 C-400 C within the operating range 159 of the solid state gas sensor module 130 are successfully maintained by supplying only 20 mW-50 mW of power to the heater 140, thus demonstrating effective heat confinement. Meanwhile, the flat curve 160b confirms that the temperature stays substantially constant at the border of the sensor region 132, thus demonstrating that thermal dissipation to neighboring devices from effects of the heater 140 is very low.

In one embodiment, power consumption of the heater 140 can be further reduced by applying a pulsed square wave signal to energize the heater 140. For example, if the heater 140 is pulsed on for 60 seconds out of every 600 seconds, or 10% of the time, the temperature will be at the target, e.g., 300 C, at least at the end of the 60-second on-period. If the SMO sensor 144 is limited to a sensing period of, for example, the last 20 seconds of the 60-second on-period, substantially similar results can be obtained using only 10% of the power that would be needed to maintain the heater 140 at 300 C continuously.

Figure 7:
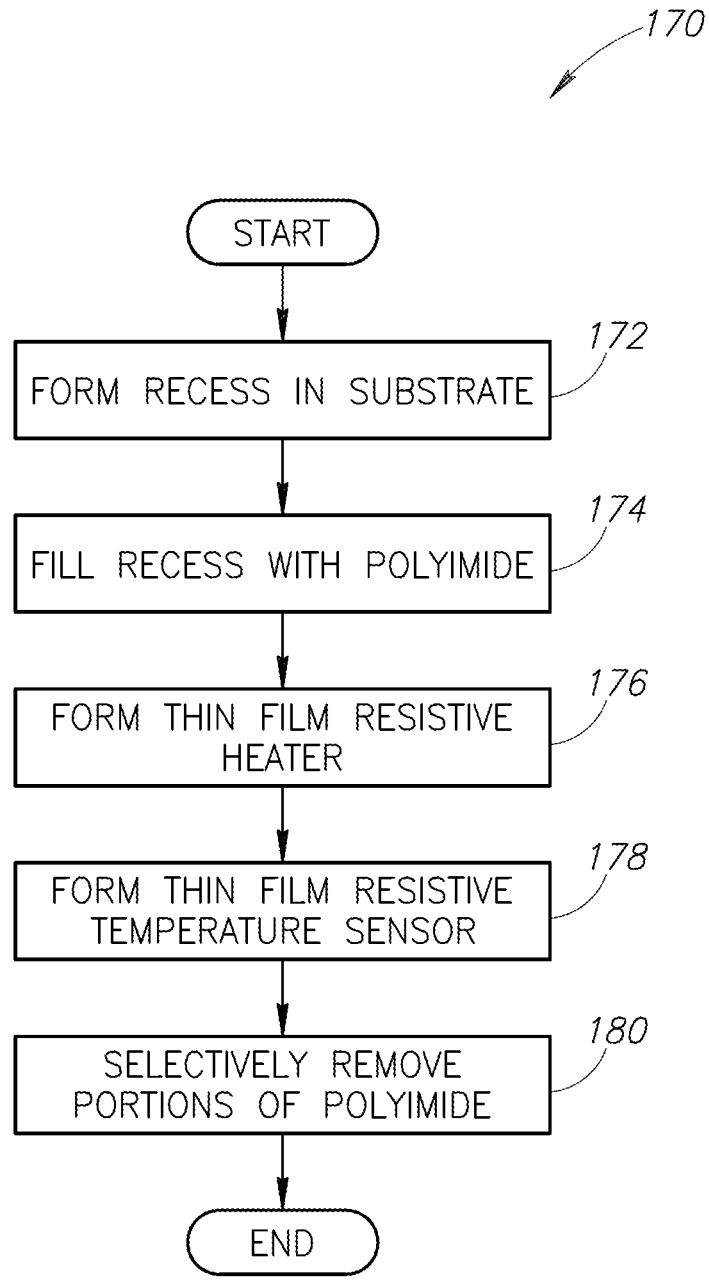
FIG. 7 is a flow diagram showing generalized steps in a method of fabricating a solid state gas sensor module as described herein.

FIG. 7 presents a flow chart showing an exemplary sequence of steps in a generalized method 170 for fabricating the solid state gas sensor module 130 as shown in FIG. 4. Cross-sectional views are shown in FIGS. 8A-10B to illustrate intermediate stages during a fabrication process having only 12 mask layers, whereas existing multi-sensor products typically have used 35-40 mask layers. Three of the 12 mask layers are metal interconnect layers made of aluminum (Al) or, alternatively, aluminum copper (AlCu).

At 172, formation of the thermal insulation structure 150 is begun by first forming a recess in the substrate 148. To form the recess, a 1 µm silicon dioxide layer 149 is deposited onto the substrate 148, which is made of glass in the embodiment described herein. The silicon dioxide layer 149 is patterned for use as a hard mask to define the recess using conventional photolithography and etching methods well known to those skilled in the art.

Figure 8A:
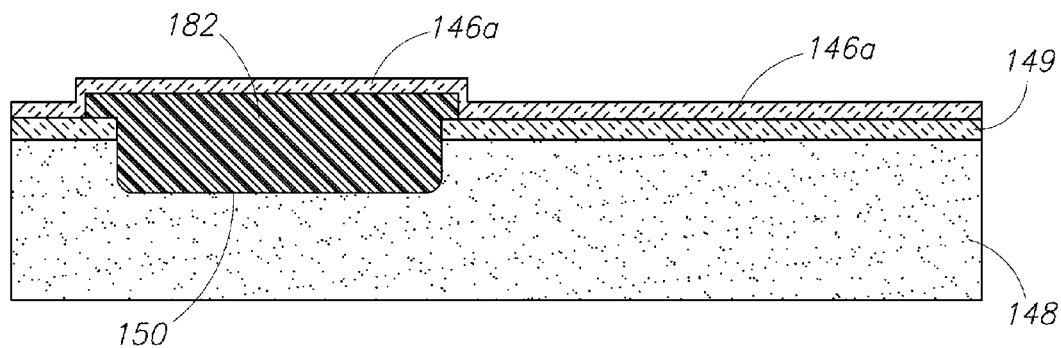
FIGS. 8A-10B are cross-sectional views of the solid state gas sensor module at various stages during fabrication according to the method shown in FIG. 7.

At 174, the recess is over-filled with a bulk polyimide 182 to a total polyimide thickness of about 4 µm. A polyimide layer formed on top of the silicon dioxide layer 149 outside the recess area is then removed by patterning and etching the polyimide using standard processing techniques. The bulk polyimide 182 within the recess is then covered with about 500 nm of a first SiN layer 146a which provides electrical insulation with a high thermal conductivity. FIG. 8A shows the solid state gas sensor module 130 after step 174 is completed.

Figure 8B:
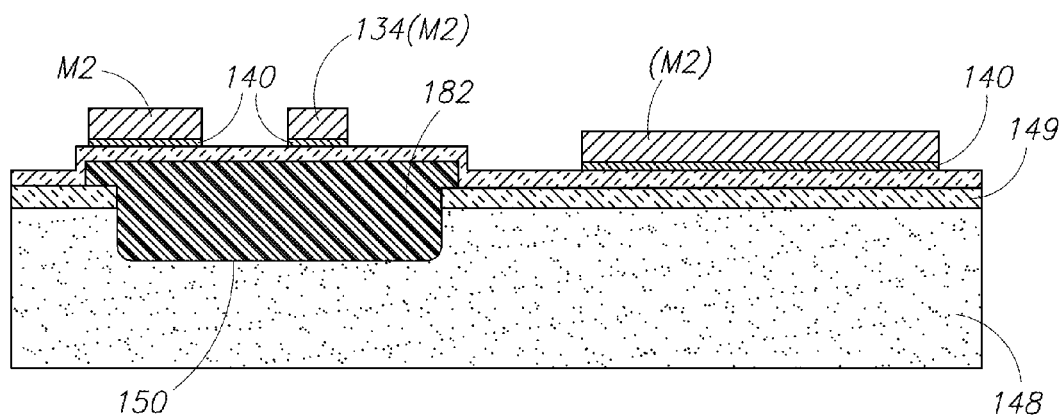
Figure 9A:
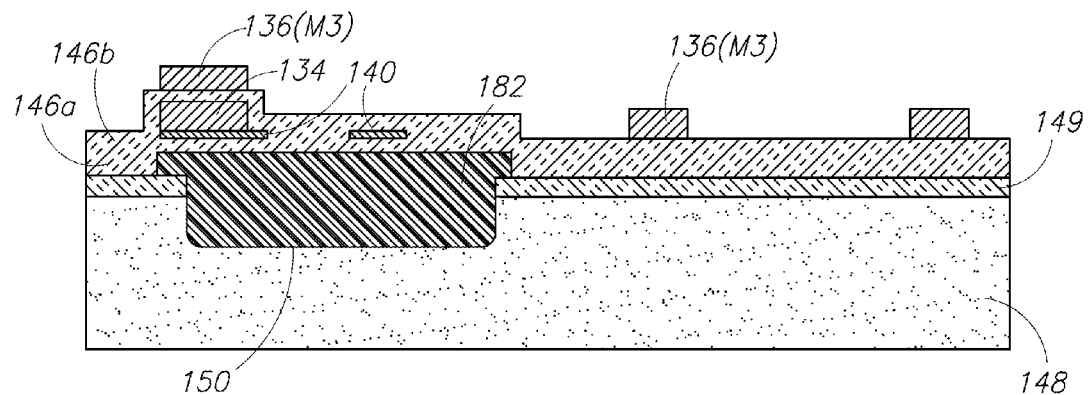

At 176, the thin film resistive heater 140 is formed. First, an 870 nm TaAl metal layer (M1) is sputter-deposited onto the first SiN layer 146a, followed by a second metal layer M2 made of 500 nm of AlCu. The AlCu and TaAl film stack is then patterned together using a standard resist mask or a hard mask (FIG. 8B). Etching can be done using either a standard wet etch or reactive ion etch process. Next, all of the aluminum structures are selectively removed except one which will provide the heater contact 134 to the resistive heater 140. Such a selective removal can be accomplished using a mask-less slope etch process that entails use of an aluminum etchant such as a solution of phosphoric acid and nitric acid. Under-cutting of AlCu and achieving a sloped profile can be done by combining a photoresist treatment with a wet etch treatment in which the ratio of phosphoric and nitric acids in the aluminum etchant is adjusted, and a surfactant is added. A sloped profile helps to manage power dissipation in the heater structure which includes a low-resistance metal (Al) adjacent to a high-resistance metal (TaAl). Next, a second dielectric SiN layer 146b is blanket deposited, followed by a via etch process to form an opening in the SiN to the heater contact 134. Then, a third 500 nm thick layer of metal, M3, is blanket deposited over the second SiN layer 146b and patterned using standard techniques to form the temperature sensor contacts 136. FIG. 9A shows the solid state gas sensor module 130 after step 176 is completed.

Figure 9B:
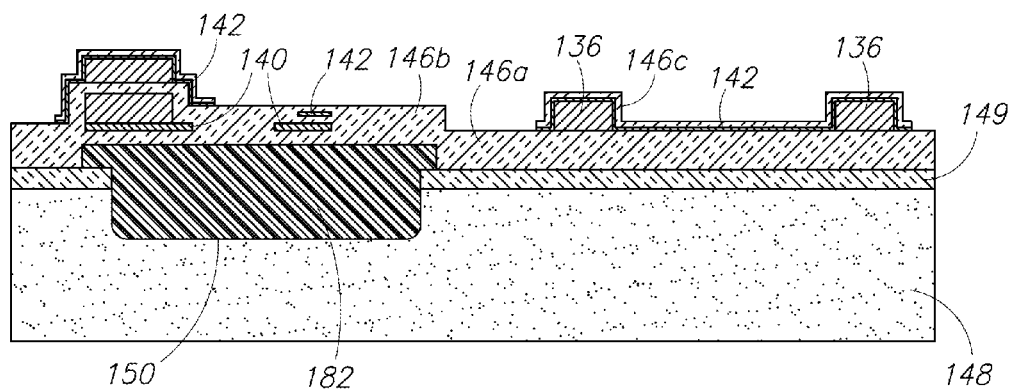
Figure 10A:
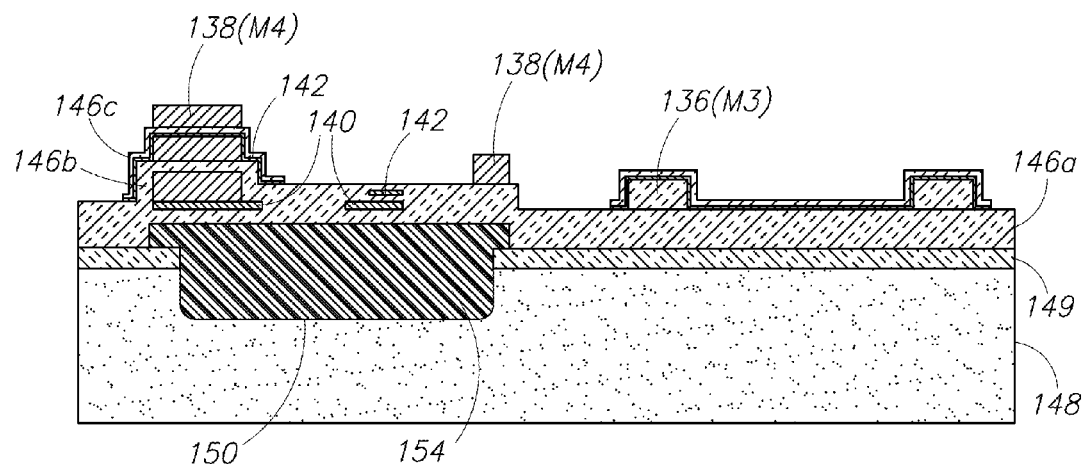

At 178, the thin film resistive temperature sensor 142 is formed. A 200-nm film of CrSi is sputter-deposited over the M3 layer, followed by 50 nm of a third SiN layer, 146c. In an alternative embodiment, 100 nm of platinum (Pt) is substituted for the CrSi film to create the temperature sensor 142. Next, the third SiN layer 146c is patterned, followed by a pad etch process to form an opening to M3. (FIG. 9B). Then, a fourth 500 nm thick layer of metal, M4, is blanket deposited over the third SiN layer 146c, and M4 is patterned using, for example, a slope etch process to form the SMO sensor contacts 138. FIG. 10A shows the solid state gas sensor module 130 after step 178 is completed.

Figure 10B:
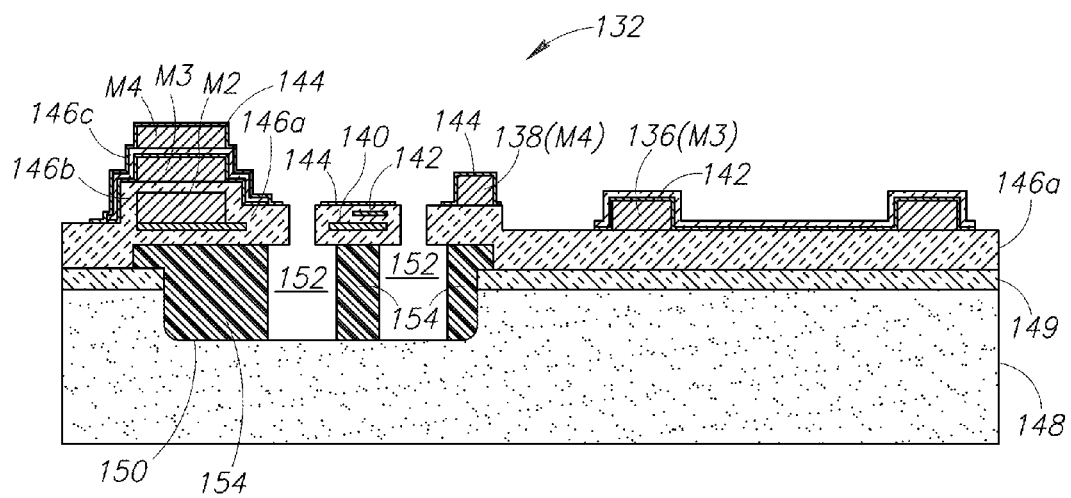

At 180, the thin film resistive SMO sensor 144 is formed. First, the SMO film is sputter-deposited over the third SiN layer 146c and the SMO film is patterned using standard processing techniques, followed by a pad etch process to form an opening to M4. Finally, the polyimide support pillars 154 are formed by etching through the SiN layers 146a, 146b, and 146c on either side of the sensor region 132 and then removing large portions of the bulk polyimide 182 using an isotropic oxygen plasma etch. Techniques suitable for pillar formation are further described in U.S. patent application Ser. No. 13/907,708 by the same inventors as the present patent application. FIG. 10B shows the solid state gas sensor module 130 after step 180 is completed.

Figure 11:
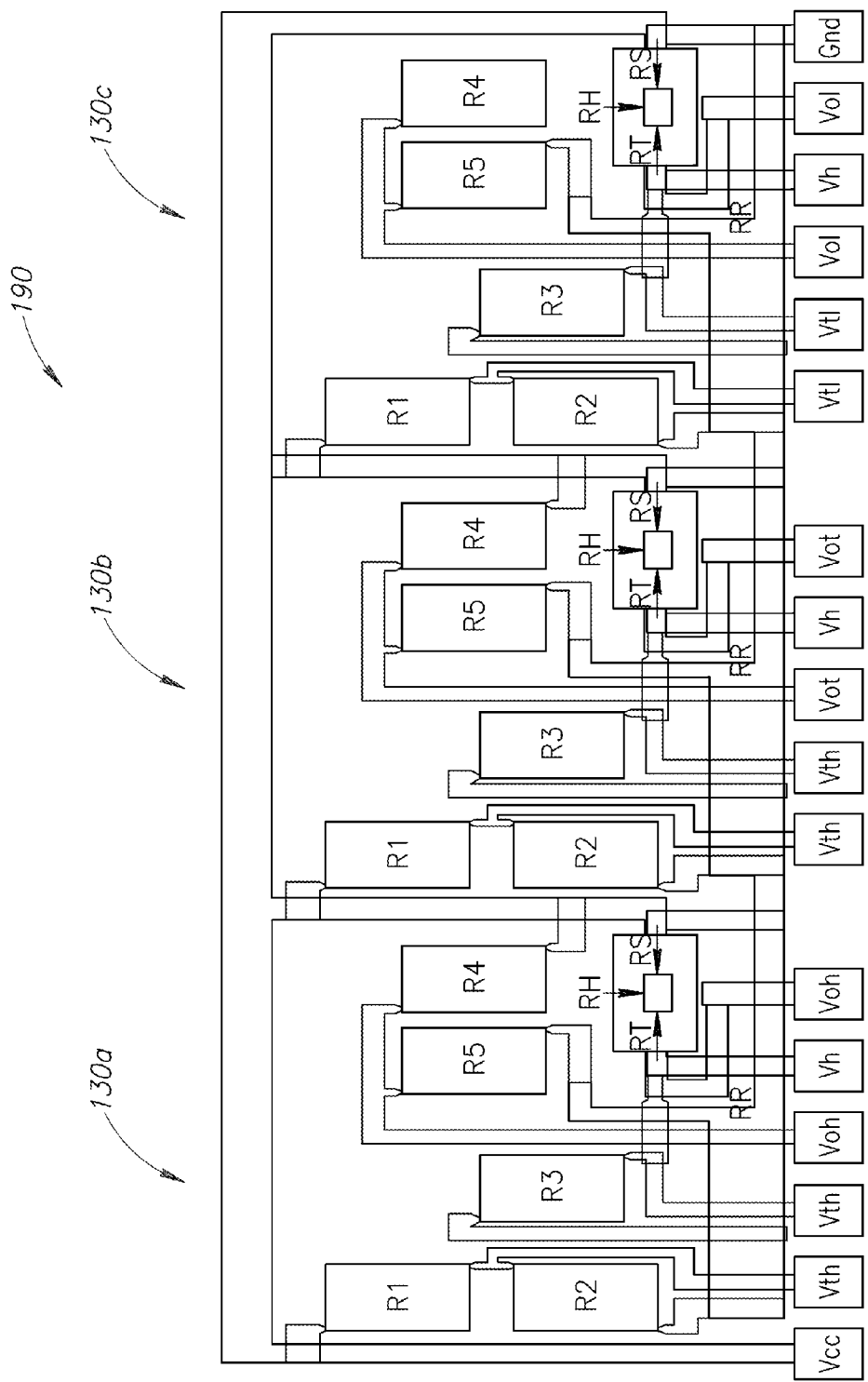
FIG. 11 is a top plan view of a circuit layout for a sensor array in which array elements are solid state gas sensor modules as described herein.

FIG. 11 shows a set of three solid state gas sensor modules, 130a, 130b, and 130c, arranged to form a multi-sensor array 190. The small area of the gas sensor module design as described above is particularly suitable for use in such an array. One way to operate the multi-sensor array 190 is to evaluate the same gas sample simultaneously at three different temperatures to achieve a more accurate result for the species concentration. For example, the solid state gas sensor module 130a can be set to the target temperature, and the solid state gas sensor modules 130b, 130c can be set to ±50 C from the target temperature, respectively. By increasing accuracy of the measurement, noise is reduced, and specificity is improved. Another way to operate the multi-sensor array 190 is to set each one of the solid state gas sensor modules to a different temperature target to detect different gas species having different thermal fingerprints. For example, the solid state gas sensor module 130a can be set at 100 C to detect ethanol while the solid state gas sensor module 130b is set at 300 C to detect CO and the gas sensor module 130c is set at 400 C to detect methane.

Figure 12:
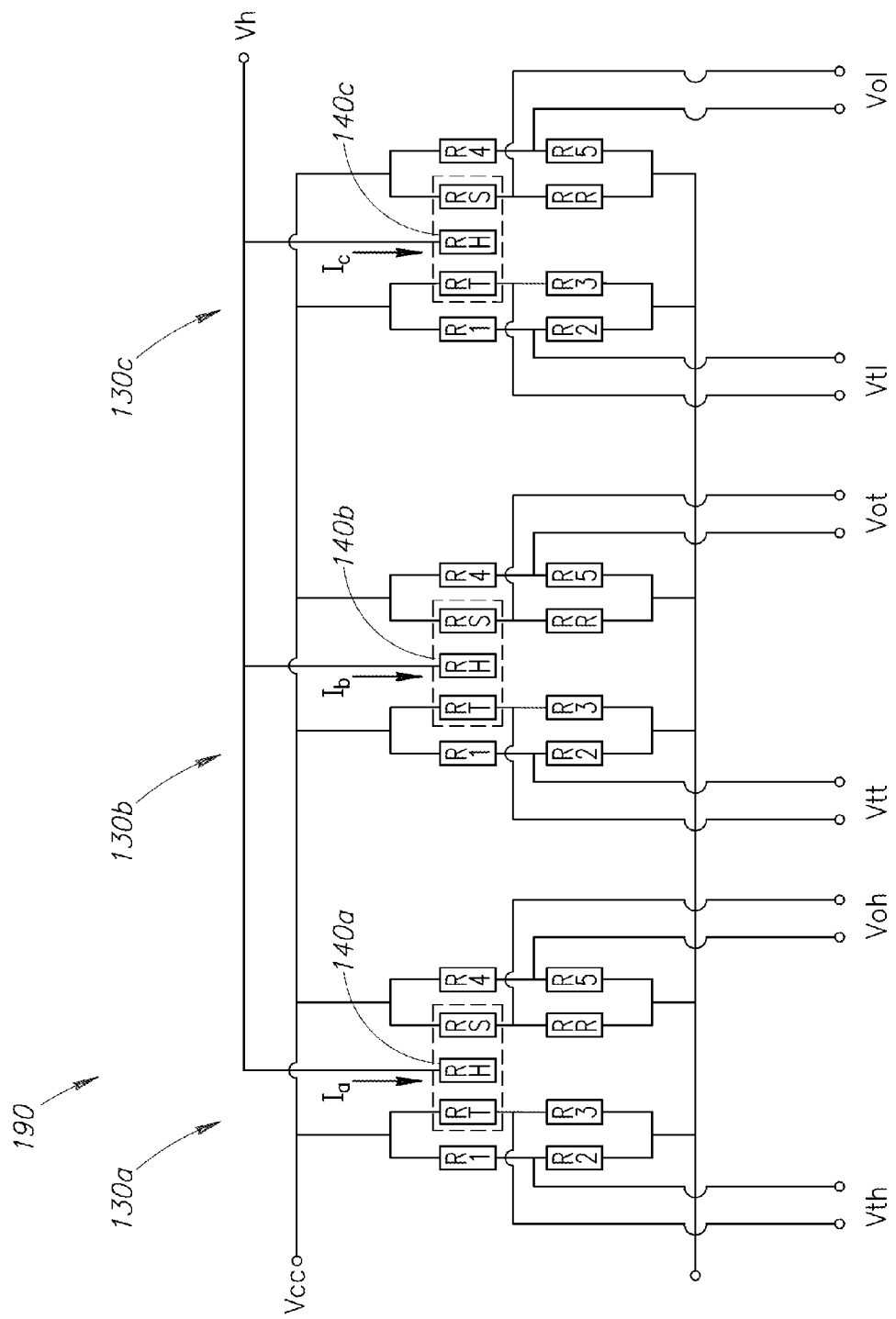
FIG. 12 is an electrical schematic diagram corresponding to the multi-sensor array shown in FIG. 11.

FIG. 12 shows an electrical schematic diagram of the multi-sensor array 190, configured as a current divider circuit to which a common voltage $V_h$ is applied. In FIG. 12, $V_{cc}$ represents a supply voltage, $V_h$ is a heater input voltage, $V_t$ is an output voltage from the temperature sensor, and $V_o$ is an output voltage from the SMO sensor. The solid state gas sensor module 130a is configured with a heater 140a having a large heater resistance $R_{ha}$, so that less current will be delivered to the solid state gas sensor module 130a according to $I=V_h/R_{ha}$. Consequently, the power dissipated in the heater 140a, given by $P=I^2R_{ha}$ will be small, producing a relatively low temperature of 100 C to detect ethanol, for example. Likewise, the solid state gas sensor module 130c is configured with a heater 140c having a small heater resistance $R_{hc}$, so that more current will be delivered to the sensor module 130c and the corresponding power dissipated in the heater 140c will be large, to produce a temperature of 500 C, to detect methane, for example. The solid state gas sensor module 130b is configured with a heater 140b having a medium heater resistance $R_{hb}$, so as to produce a temperature of 300 C, to detect carbon monoxide, for example.

Figure 13:
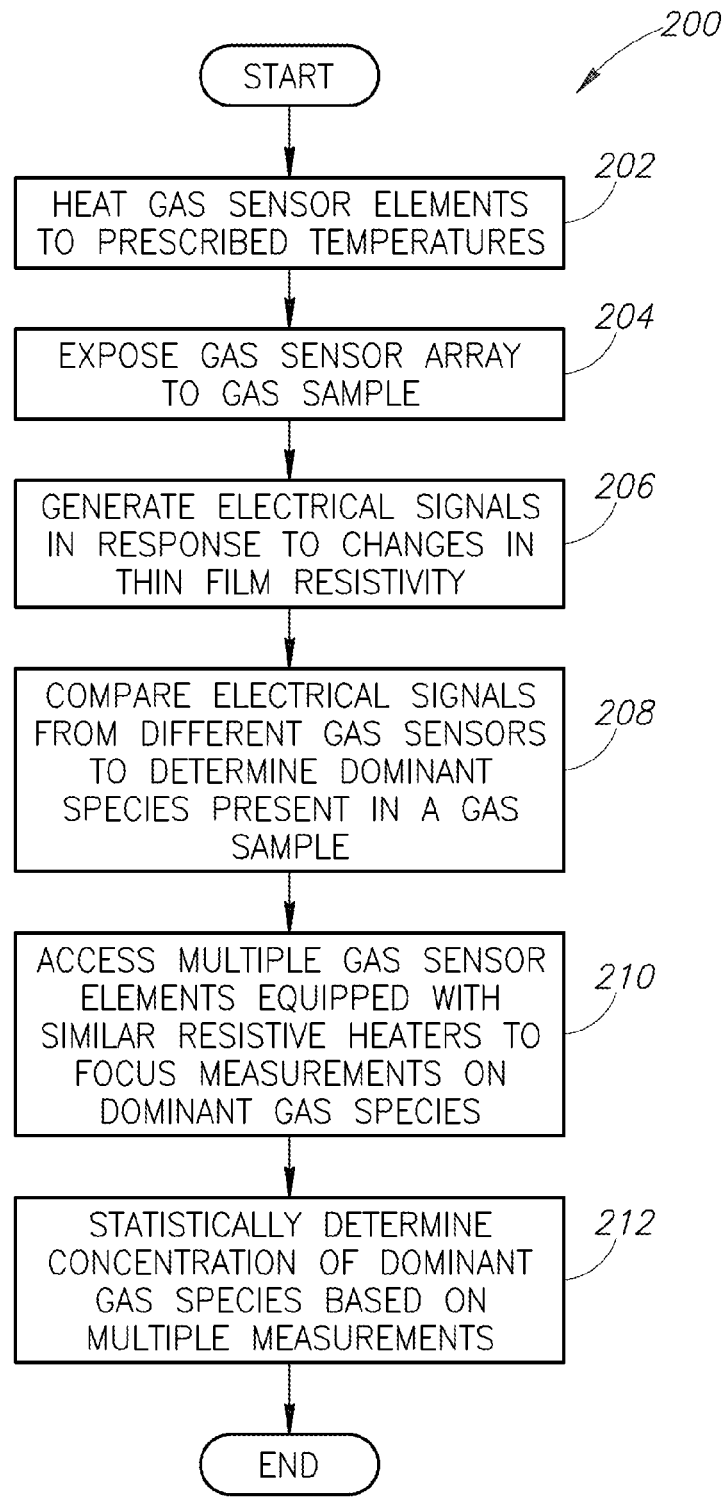
FIG. 13 is a flow diagram showing generalized steps in an exemplary method of operating the multi-sensor array shown in FIGS. 11 and 12.

Either one of the two operating schemes described above can be carried out using a 1×3 multi-sensor array 190, which occupies a surface area of about 1 mm². Alternatively, a 3×3 sensor array allows for redundant measurements at each of three different temperatures, effectively producing more accurate data for each of three different gas species. However, a 3×3 sensor array requires more power and takes up more chip real estate. A 3×3 sensor array like the ones described herein occupies a surface area of about 3 mm². Another way to operate the multi-sensor array 190 is to perform a rough measurement to determine the dominant gas species in a sample, and then to tune all of the gas sensors to measure the dominant species. Generalized steps in such a thermo-cycling method 200 are outlined in FIG. 13 as follows:

At 202, SMO sensors 144a, 144b, and 144c are heated to different prescribed temperatures to target three different gas species thought to be present in the ambient environment.

At 204, the multi-sensor array 190 is exposed to a gas sample of the ambient environment.

At 206, electrical signals are generated by the SMO sensors 144a, 144b, and 144c in response to changes in thin film resistivity of the common SMO material.

At 208, the electrical signals from the three different SMO sensors are compared to determine which of the three gas species is the dominant gas species in the gas sample.

At 210, the heaters 140a, 140b, and 140c are all tuned to the same temperature associated with the dominant gas species.

At 212, all three SMO sensors 144a, 144b, and 144c are used to measure the dominant gas species so that statistics can be calculated to determine with greater accuracy the concentration of the dominant gas species.

Figure 14:
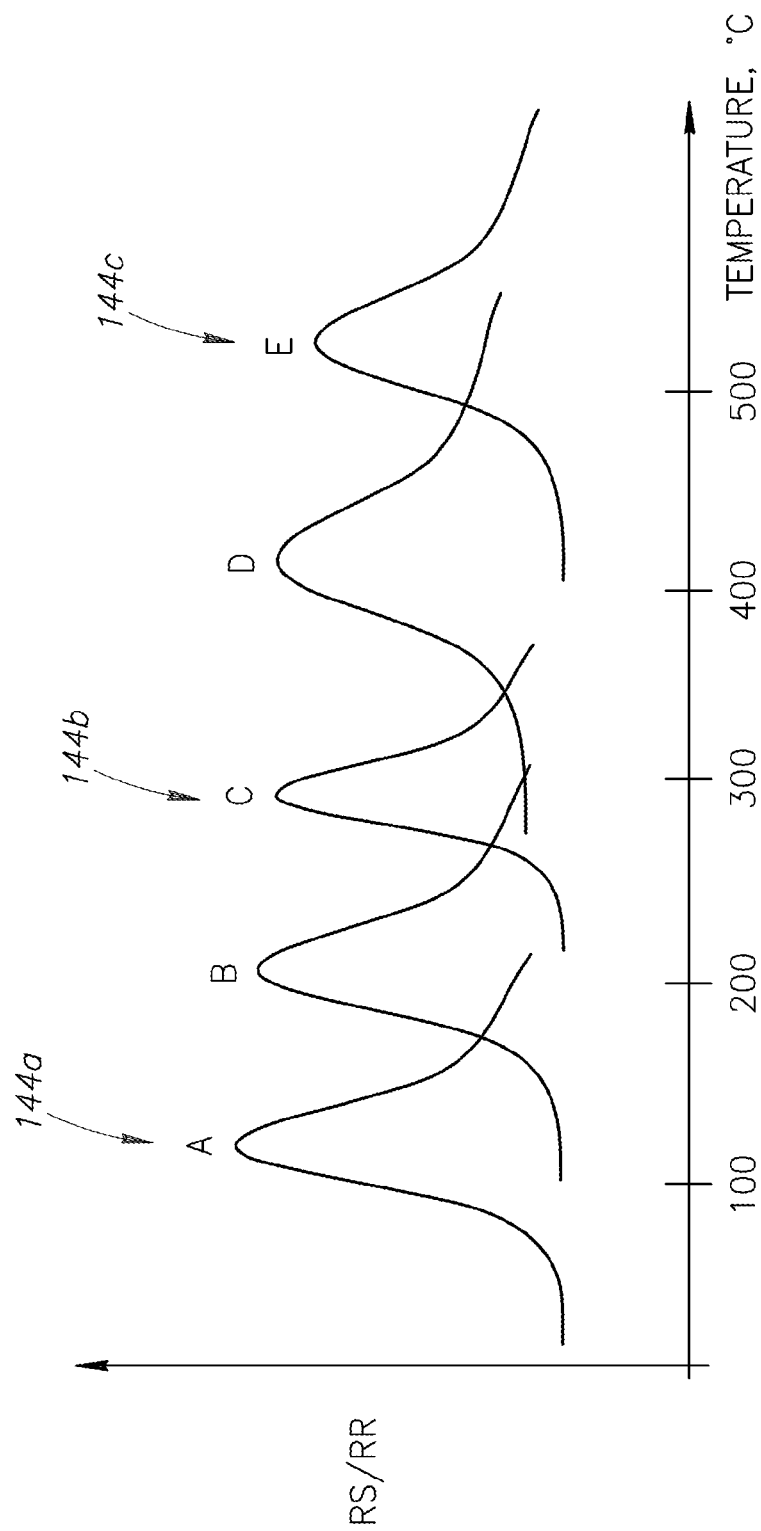
FIG. 14 is a plot of SMO gas sensor responses to different gas species as a function of temperature.

With reference to FIG. 14, in steps 202-206, depending on the exact temperatures of the heaters, the common SMO material used in the SMO sensors may respond to several different gas species a, b, c, d, and e at the same time, i.e., the species differentiation may not be distinct. For example, if the operating temperatures of the different heaters differ by 100 C, the SMO closest to a heater set at 300 C, e.g., SMO 144b, may be influenced somewhat by gases b and d that are detectable at 200 C and 400 C respectively, but not influenced significantly by gases a and e that are detectable at 100 C and 500 C, respectively. As the operating temperatures are brought closer together, the species differentiation becomes worse. This is because statistical distributions associated with a particular SMO material response at different temperatures are not mutually exclusive, but instead have some amount of overlap, as illustrated in FIG. 14. Consequently, for better differentiation of gas species, it may be desirable to operate adjacent SMO sensors 144a and 144c at 100 C to detect gas species a, and at 500 C to detect gas species e, and to forego the measurements of species b and d at 200 C and 400 C, respectively. Alternatively, different SMO materials could be used to improve the differentiation of gas species within a narrower temperature range. Since, in the present semiconductor implementation, it is not feasible to incorporate multiple SMO materials into the multi-sensor array 190, it is therefore desirable to operate with temperatures for adjacent array elements being spaced apart by no less than 50 C.

Figure 15A:
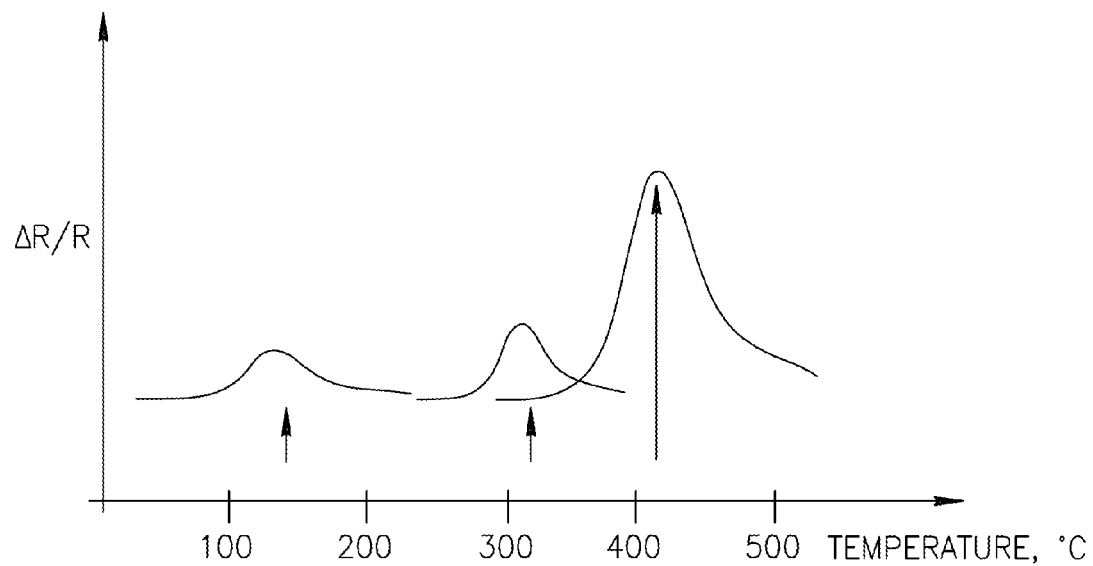
FIGS. 15A-15C are plots of SMO gas sensor responses to different gas species as a function of temperature when operated according to the method shown in FIG. 13.
Figure 15B:
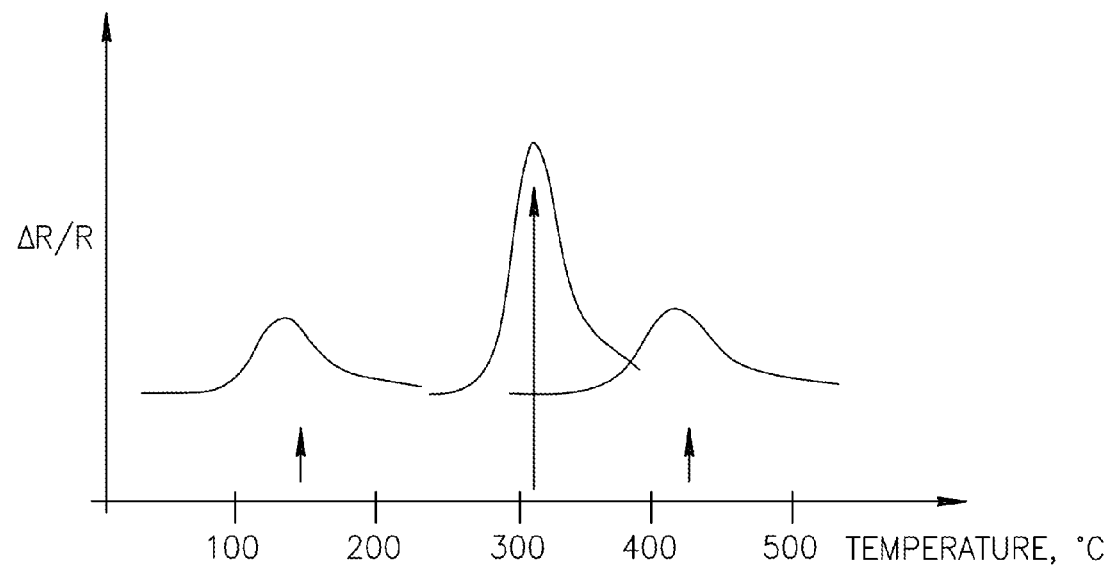
Figure 15C:
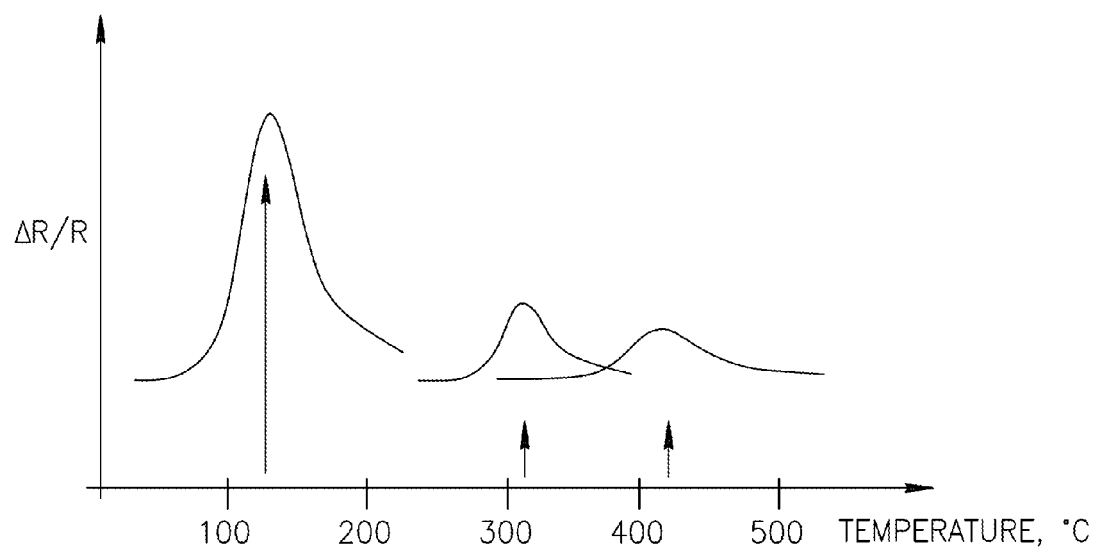

On the other hand, while entirely different SMO materials may not be feasible, implanting different portions of the SMO film with different dopants is a practical alternative that allows operating at a common temperature while still achieving a high degree of gas species differentiation. For example, in a 3×3 sensor array, one row of sensors may be fabricated by doping the $SnO_2$ film with platinum to detect $H_2SO_4$, while a second row of SMO sensors is doped with palladium to detect CO, and the third row of SMO sensors can be doped with gold. The doping can be accomplished during an in-situ plasma vapor deposition (PVD) process as the $SnO_2$ is being formed, or by implant doping after the $SnO_2$ film is deposited. With doped SMO sensor films, the ability to differentiate gas species improves as illustrated in FIGS. 15A, 15B, and 15C. For example, in FIG. 15A, the SMO sensor response to methane at 400 C is significantly greater than the response to CO at 325 C or ethanol at 150 C; similarly, in FIG. 15B, the SMO sensor response to CO at 325 C is significantly greater than the response to methane at 400 C or ethanol at 150 C; and in FIG. 15C, the SMO sensor response to ethanol at 150 C is significantly greater than the response to CO at 325 C or methane at 400 C.

The structure, size, and thermal properties of the solid state gas sensor modules 130 as described herein thus permit flexibility in operation of the sensor array 190.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

It will be appreciated that, although specific embodiments of the present disclosure are described herein for purposes of illustration, various modifications may be made without departing from the spirit and scope of the present disclosure. Accordingly, the present disclosure is not limited except as by the appended claims.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
a substrate;
a thin film resistive semiconductor metal oxide (SMO) sensor over the substrate;
a resistive heater over the substrate and disposed adjacent to the thin film resistive SMO sensor;
a resistive temperature sensor over the substrate and disposed adjacent to the resistive heater; and a thermal insulation structure in the substrate between the resistive heater and the substrate, the thermal insulation structure including support pillars surrounded by an air gap.

2. The device of claim 1, further comprising an application specific integrated circuit (ASIC) communicatively coupled to the thin film resistive SMO sensor, the resistive heater, and the resistive temperature sensor.

3. The device of claim 2 wherein the ASIC is on the substrate, and the thin film resistive SMO sensor is spaced from the substrate by the ASIC.

4. The device of claim 2 wherein the ASIC includes a microprocessor communicatively coupled to a non-transitory computer-readable memory having processor-executable instructions stored thereon, the microprocessor programmed to receive signals from the resistive temperature sensor and the thin film resistive SMO sensor.

5. The device of claim 4 wherein the microprocessor is further programmed to transmit control signals to the resistive heater.

6. The device of claim 5 wherein the control signals are generated in response to temperature data received from the resistive temperature sensor.

7. The device of claim 2 wherein an active sensing area of the thin film resistive SMO sensor is approximately 50×50 square microns.

8. The device of claim 7, further comprising a cap covering a perimeter of the ASIC, wherein a surface area of the ASIC that includes the active sensing area of the thin film resistive SMO sensor is exposed to an ambient environment.

9. The device of claim 1 wherein the resistive heater is equipped with a thin film resistor configured to heat the thin film resistive SMO sensor to a temperature within the range of about 100 C-400 C while consuming less than 50 mW of power.

10. The device of claim 1 wherein the substrate is made of glass.

11. The device of claim 1 wherein the substrate is made of silicon.

12. The device of claim 1 wherein the support pillars are made of polyimide.

13. The device of claim 1 wherein the resistive heater includes a metal thin film made of TaAl.

14. The device of claim 1 wherein the thin film resistive SMO sensor includes a metal thin film that includes tin oxide ($SnO_2$).

15. The device of claim 1 wherein the resistive temperature sensor includes a metal thin film made of CrSi.

16. The device of claim 1 wherein the resistive temperature sensor includes a metal thin film made of Pt.

17. The device of claim 1 wherein the resistive heater is activated by a pulsed power signal that remains in an on state for about 10% of a pulse period time interval.

18. A method of fabricating a solid state gas sensor on a substrate, the method comprising:
forming a recess in the substrate;
filling the recess with a support material;
forming a thin film resistive semiconductor metal oxide (SMO) sensor on the support material, the thin film resistive SMO sensor including a material having a variable resistance that changes with temperature;
forming a thin film resistive heater on the support material and adjacent to the thin film resistive SMO sensor, the thin film resistive heater configured to transfer heat to the thin film resistive SMO sensor in response to an applied voltage;
forming a thin film resistive temperature sensor on the support material adjacent to the heater;
forming electrical contacts to the thin film resistive SMO sensor, the thin film resistive heater, and the thing film resistive temperature sensor; and
selectively removing portions of the support material from the recess to form air gaps that thermally isolate the solid state gas sensor.

19. The method of claim 18 wherein remaining portions of the support material form pillars positioned to structurally support the thin film resistive heater, the thin film resistive SMO sensor, and the thin film resistive temperature sensor.

20. The method of claim 18 wherein the support material is polyimide.

21. A system, comprising:
a substrate,
a plurality of solid state gas sensor modules on the substrate, each of the plurality of solid state gas sensor modules, including:
a thin film resistive semiconductor metal oxide (SMO) sensor on the substrate;
a resistive heater on the substrate and disposed adjacent to the thin film resistive SMO sensor;
a resistive temperature sensor on the substrate and disposed adjacent to the resistive heater; and
a thermal insulation structure in the substrate between the resistive heater and the substrate, the thermal insulation structure including support pillars surrounded by an air gap.

22. The system of claim 21, further comprising:
control signal lines coupled to the plurality of the solid state gas sensor modules, wherein each of the plurality of solid state gas sensor modules further includes:
a plurality of bridge resistors each having a fixed resistance;
a temperature output signal line coupled to the resistive temperature sensor; and
a gas sensor output signal line coupled to the thin film resistive SMO sensor.

23. The system of claim 22 wherein the control signal lines include a heating voltage line, a power supply voltage line, and a ground line.

24. The system claim 21 wherein the plurality of solid state gas sensor modules has a total footprint area less than 2.5 mm$^2$.

25. The system of claim 21 wherein the resistive heater is configured to heat the thin film resistive SMO sensor to a selected temperature at which the thin film resistive SMO sensor is predominantly sensitive to a selected gas species.

26. The system of claim 25 wherein the selected gas species is one of ethanol vapor, carbon monoxide (CO), methane ($CH_4$), hydrogen sulfide ($H_2S$), and sulfur dioxide ($SO_2$).

27. The system of claim 21 wherein the thin film resistive SMO sensor includes dopants.

28. The system of claim 27 wherein the thin film resistive SMO sensor is doped with one or more of palladium (Pd), platinum (Pt), or silver (Ag).

* * * * *